(12) United States Patent
Oikawa et al.

(10) Patent No.: US 10,588,856 B2
(45) Date of Patent: Mar. 17, 2020

(54) ORALLY DISINTEGRATING TABLET COATED WITH FILM

(71) Applicant: SAWAI PHARMACEUTICAL CO., LTD., Osaka (JP)

(72) Inventors: Michinori Oikawa, Osaka (JP); Hiroyuki Yamamoto, Osaka (JP); Hiroaki Kikuoka, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/233,534

(22) Filed: Aug. 10, 2016

(65) Prior Publication Data

US 2016/0346199 A1 Dec. 1, 2016

Related U.S. Application Data

(63) Continuation of application No. PCT/JP2015/053880, filed on Feb. 12, 2015.

(30) Foreign Application Priority Data

Feb. 12, 2014 (JP) .................................. 2014-024524

(51) Int. Cl.
*A61K 9/00* (2006.01)
*A61K 9/28* (2006.01)

(52) U.S. Cl.
CPC ............ *A61K 9/0056* (2013.01); *A61K 9/284* (2013.01); *A61K 9/2853* (2013.01); *A61K 9/2866* (2013.01)

(58) Field of Classification Search
CPC .... A61K 9/0056; A61K 9/2866; A61K 9/284; A61K 9/2853
See application file for complete search history.

(56) References Cited

U.S. PATENT DOCUMENTS

| | | | | |
|---|---|---|---|---|
| 5,807,580 | A * | 9/1998 | Luber .................. | A61K 9/2813 424/480 |
| 6,277,409 | B1 * | 8/2001 | Luber .................. | A61K 9/282 424/476 |
| 7,883,722 | B2 * | 2/2011 | Bar-Shalom ........ | A61K 9/0092 424/467 |
| 2002/0119196 | A1 * | 8/2002 | Parikh ................. | A61K 9/0056 424/472 |
| 2003/0044446 | A1 * | 3/2003 | Moro .................... | A61K 9/006 424/426 |
| 2008/0138429 | A1 * | 6/2008 | Humar ................ | A61K 9/2009 424/494 |
| 2010/0330150 | A1 * | 12/2010 | Venkatesh ........... | A61K 9/2081 424/439 |
| 2012/0058186 | A1 | 3/2012 | Takaki et al. | |
| 2012/0189693 | A1 * | 7/2012 | Dick .................... | A61J 3/10 424/465 |
| 2013/0189360 | A1 * | 7/2013 | Sakamoto ........... | A61K 9/2081 424/465 |

FOREIGN PATENT DOCUMENTS

| | | | |
|---|---|---|---|
| EP | 2316433 A1 | 5/2011 | |
| EP | 2415466 A1 | 2/2012 | |
| JP | 2001-192344 A | 7/2001 | |
| JP | 2005-519924 A | 7/2005 | |
| JP | 2008-280316 A | 11/2008 | |
| JP | 2009-5680 A | 1/2009 | |
| JP | 2010-248106 | * 11/2010 | ............... A61K 9/30 |
| JP | 2010-248106 A | 11/2010 | |
| JP | 2013-155148 A | 8/2013 | |
| JP | 2013-177438 A | 9/2013 | |
| WO | 03/066029 A2 | 8/2003 | |
| WO | 2010/113841 A1 | 10/2010 | |
| WO | 2014/157264 A1 | 10/2014 | |

OTHER PUBLICATIONS

Machine translation of JP2010-248106.*
Pharmacoat (Year: 2019).*
Pharmacoat II (Year: 2005).*
Rungsinee Sothornvit & John M. Krochta, Plasticizers in edible films and coatings in Innovations in Food Packaging 403-433 (Food Science and Technology 2005) (Year: 2005).*
International Search Report dated Mar. 31, 2015 for Corresponding PCT Application PCT/JP2015/053880 with English Translation.
Written Opinion of the International Search Authority dated Mar. 31, 2015 for Corresponding PCT Application PCT/JP2015/053830.
English Translation of Written Opinion of the International Search Authority dated Mar. 31, 2015 for corresponding PCT Application PCT/JP2015/053880 which was previously submitted on Aug. 10, 2017.
Extended European search report for the counter European Patent application No. 15748550.9 dated Aug. 16, 2017.
Japanese Office Action dated Jun. 19, 2018 for the corresponding Japanese patent application No. 2015-562867, citing above reference and with partial English translation.
Japanese Office Action dated Jan. 29, 2019 for corresponding Japanese Patent Application No. 2015-562867, with partial English Translation, citing the above references.

* cited by examiner

*Primary Examiner* — Sean M Basquill
(74) *Attorney, Agent, or Firm* — Hauptman Ham, LLP

(57) ABSTRACT

Provided is an orally disintegrating tablet coated with film that allows the time elapsed before a film thereof dissolves to be shorter, has a good feel when the tablet is taken, and is capable of being easily mass-produced. The orally disintegrating tablet coated with film is coated with a film coating composition, the film coating composition comprises a water-soluble and ethanol-insoluble film coating base; and at least one plasticizer selected from the group consisting of propylene glycol and polyethylene glycol in a liquid or semisolid state at room temperature. The orally disintegrating tablet coated with film is coated with a film coating composition, the film coating composition comprises a water-soluble and ethanol-insoluble film coating base; and at least one plasticizer selected from the group consisting of propylene glycol and polyethylene glycol in a liquid or semisolid state at room temperature, and contains the plasticizer in 10% by weight or more with respect to a weight of the film coating base.

4 Claims, 7 Drawing Sheets

FIG. 1

| Additive | | Example 1 Blending amount (mg) | Example 2 Blending amount (mg) | Example 3 Blending amount (mg) | Comparative Example 1 Blending amount (mg) | Comparative Example 2 Blending amount (mg) |
|---|---|---|---|---|---|---|
| Film base | HPMC | 2.27 | | | | |
| | PVA | | 2.27 | | | |
| | Kollicoat IR | | | 2.27 | | |
| | HPC | | | | 2.27 | |
| | PVP | | | | | 2.27 |
| Plasticizer | Macrogol 400 | 2.27 | 2.27 | 2.27 | 2.27 | 2.27 |
| Excipient | Erythritol | 0.50 | 0.50 | 0.50 | 0.50 | 0.50 |
| Disintegrant | Crospovidone | 0.06 | 0.06 | 0.06 | 0.06 | 0.06 |
| Lubricant | Talc | 0.40 | 0.40 | 0.40 | 0.40 | 0.40 |
| Corrigent | Sucralose | 0.03 | 0.03 | 0.03 | 0.03 | 0.03 |
| Titanium dioxide | TiO$_2$ | 0.06 | 0.06 | 0.06 | 0.06 | 0.06 |
| Coloring agent | Yellow ferric oxide | Very small amount | Very small amount | Very small amount | Very small amount | Very small amount |
| | Blue No. 2 Al lake | Very small amount | Very small amount | Very small amount | Very small amount | Very small amount |
| Total | | 5.59 | 5.59 | 5.59 | 5.59 | 5.59 |
| Coatability | | Good | Good | Good | Not acceptable | Not acceptable |
| Pairing at the time of coating | | Not observed | Not observed | Not observed | Observed | Observed |
| Mouth-feel of the film when the tablet is taken | | No problem | No problem | No problem | - | - |
| Bitterness of the film | | Not observed | Not observed | Not observed | - | - |
| Hardness | Uncoated orally disintegrating tablet (kg) | 6.0 | 6.0 | 6.0 | - | - |
| | Coated orally disintegrating tablet (kg) | 6.6 | 8.1 | 6.9 | - | - |
| | Increasing ratio(%) | 10 | 35 | 15 | - | - |
| Dissolving time of the film (s) | | 6 - 7 | 5 - 6 | 5 - 6 | - | - |

FIG. 2

| | Additive | Example 1 Blending amount (mg) | Example 4 Blending amount (mg) | Example 5 Blending amount (mg) | Comparative Example 3 Blending amount (mg) | Comparative Example 4 Blending amount (mg) | Comparative Example 5 Blending amount (mg) | Comparative Example 6 Blending amount (mg) | Comparative Example 7 Blending amount (mg) | Comparative Example 8 Blending amount (mg) |
|---|---|---|---|---|---|---|---|---|---|---|
| Film base | HPMC | 2.27 | 2.27 | 2.27 | 2.27 | 2.27 | 2.27 | 2.27 | 2.27 | 1.13 |
| | Macrogol 400 | 2.27 | | | | | | | | |
| | Macrogol 1500 | | 2.27 | | | | | | | |
| Plasticizer | PG | | | 2.27 | | | | | | |
| | Macrogol 6000 | | | | 2.27 | | | | | |
| | triacetin | | | | | 2.27 | | | | |
| | triethyl citrate | | | | | | 2.27 | | | |
| | glycerin | | | | | | | 2.27 | | |
| | D-sorbitol | | | | | | | | | |
| Excipient | Erythritol | 0.50 | 0.50 | 0.50 | 0.50 | 0.50 | 0.50 | 0.50 | 0.50 | 0.50 |
| Disintegrant | Crospovidone | 0.06 | 0.06 | 0.06 | 0.06 | 0.06 | 0.06 | 0.06 | 0.06 | 0.06 |
| Lubricant | Talc | 0.40 | 0.40 | 0.40 | 0.40 | 0.40 | 0.40 | 0.40 | 0.40 | 0.40 |
| Corrigent | Sucralose | 0.03 | 0.03 | 0.03 | 0.03 | 0.03 | 0.03 | 0.03 | 0.03 | 0.03 |
| Titanium dioxide | $TiO_2$ | 0.06 | 0.06 | 0.06 | 0.06 | 0.06 | 0.06 | 0.06 | 0.06 | 0.06 |
| Coloring agent | Yellow ferric oxide | Very small amount | Very small amount | Very small amount | Very small amount | Very small amount | Very small amount | Very small amount | Very small amount | Very small amount |
| | Blue No. 2 Al lake | Very small amount | Very small amount | Very small amount | Very small amount | Very small amount | Very small amount | Very small amount | Very small amount | Very small amount |
| | Total | 5.59 | 5.59 | 5.59 | 5.59 | 5.59 | 5.59 | 5.59 | 5.59 | 5.59 |
| | Coatability | Good | Good | Good | Good | Good | Good | Good | Good | Not Observed |
| | Pairing at the time of coating | Not observed | Not observed | Not observed | Not observed | Not observed | Not observed | Not observed | Not observed | Observed |
| | Temperature limitation at the time of coating | No | No | No | No | No | No | No | No | No |
| | Mouth-feel of the film when the tablet is taken | No problem | No problem | No problem | Slightly unpleasant | Unpleasant | Unpleasant | Slightly unpleasant | Slightly unpleasant | - |
| | Bitterness of the film | Not observed | Not observed | Not observed | Not observed | Observed | Observed | Not observed | Not observed | - |
| Hardness | Uncoated orally disintegrating tablet (kg) | 6.0 | 6.0 | 6.0 | 6.0 | 6.0 | 6.0 | 6.0 | 6.0 | - |
| | Coated orally disintegrating tablet (kg) | 6.6 | 7.4 | 9.1 | 7.2 | 9.3 | 7.9 | 7.0 | 7.7 | - |
| | Increasing ratio(%) | 10 | 23 | 52 | 20 | 55 | 32 | 17 | 28 | - |
| | Dissolving time of the film (s) | 6 - 7 | 5 - 6 | 4 - 5 | 7 - 8 | 9 - 10 | 6 - 7 | 7 - 8 | 6 - 7 | - |

FIG. 3

| Additive | | Blending amount (mg) | Blending amount (mg) | Blending amount (mg) | Blending amount (mg) |
|---|---|---|---|---|---|
| Film base | HPMC | 4.14 | 3.78 | 3.49 | 2.27 |
| Plasticizer | Macrogol 400 | 0.40 | 0.76 | 1.05 | 2.27 |
| Lubricant | Talc | 0.40 | 0.40 | 0.40 | 0.40 |
| Titanium dioxide | TiO$_2$ | 0.06 | 0.06 | 0.06 | 0.06 |
| Total | | 5.00 | 5.00 | 5.00 | 5.00 |
| Ratio of the plasticizer to the base | | 9.7% | 20.1% | 30.1% | 100.0% |
| Coatability | | Good | Good | Good | Good |
| Pairing at the time of coating | | Not observed | Not observed | Not observed | Not observed |
| Temperature limitation at the time of coating | | No | No | No | No |
| Bitterness of the film | | No problem | No problem | No problem | No problem |
| Hardness | Uncoated orally disintegrating tablet (kg) | 6.0 | 6.0 | 6.0 | 6.0 |
| | Coated orally disintegrating tablet (kg) | 9.4 | 9.1 | 8.2 | 6.7 |
| | Increasing ratio(%) | 57 | 52 | 37 | 12 |
| Dissolving time of the film (s) | | 10 - 11 | 9 - 10 | 7 - 8 | 7 - 8 |

FIG. 4

| | | Example 1 | Example 6 | Example 7 | Example 5 | Example 8 | Example 9 | Example 10 | Example 11 | Example 12 | Example 13 |
|---|---|---|---|---|---|---|---|---|---|---|---|
| | Additive | Blending amount (mg) | Blending amount (mg) | Blending amount (mg) | Blending amount (mg) | Blending amount (mg) | Blending amount (mg) | Blending amount (mg) | Blending amount (mg) | Blending amount (mg) | Blending amount (mg) |
| Film base | HPMC | 2.270 | 1.130 | 1.130 | 2.270 | 1.130 | 1.130 | 1.130 | 1.130 | 1.130 | 3.780 |
| Plasticizer | Macrogol 400 | 2.270 | 3.410 | 2.842 | 2.270 | 3.410 | 3.350 | 2.842 | 1.705 | 1.705 | 0.760 |
| | PG | | | | | | | | | | |
| | glycerin | | | 0.568 | | | 0.060 | 0.568 | 1.705 | | |
| Excipient | Erythritol | 0.500 | 0.500 | 0.500 | 0.500 | 0.500 | 0.500 | 0.500 | 0.500 | 0.500 | 0.500 |
| | maltose | | | | | | | | | | |
| | D-mannitol | | | | | | | | | 1.705 | |
| Disintegrant | Crospovidone | 0.060 | 0.060 | 0.060 | 0.060 | 0.060 | 0.060 | 0.060 | 0.060 | 0.060 | 0.060 |
| Lubricant | Talc | 0.400 | 0.400 | 0.400 | 0.400 | 0.400 | 0.400 | 0.400 | 0.400 | 0.400 | 0.400 |
| Corrigent | Sucralose | 0.030 | 0.030 | 0.030 | 0.030 | 0.030 | 0.030 | 0.030 | 0.030 | 0.030 | 0.030 |
| Titanium dioxide | TiO₂ | 0.060 | 0.060 | 0.060 | 0.060 | 0.060 | 0.060 | 0.060 | 0.060 | 0.060 | 0.060 |
| Coloring agent | Yellow ferric oxide | Very small amount | Very small amount | Very small amount | Very small amount | Very small amount | Very small amount | Very small amount | Very small amount | Very small amount | Very small amount |
| | Blue No. 2 Al lake | Very small amount | Very small amount | Very small amount | Very small amount | Very small amount | Very small amount | Very small amount | Very small amount | Very small amount | Very small amount |
| | Total | 5.590 | 5.590 | 5.590 | 5.590 | 5.590 | 5.590 | 5.590 | 5.590 | 5.590 | 5.590 |
| Ratio of the plasticizer to the base | | 100.0% | 301.8% | 301.8% | 100.0% | 301.8% | 301.8% | 301.8% | 301.8% | 150.9% | 20.1% |
| Ratio of Macrogol 400 or PG to the base | | 100.0% | 301.8% | 251.5% | 100.0% | 301.8% | 296.5% | 251.5% | 150.9% | 150.9% | 20.1% |
| Coatability | | Good | Good | Good | Good | Good | Good | Good | Good | Good | Good |
| Pairing at the time of coating | | Not observed | Not observed | Not observed | Not observed | Not observed | Not observed | Not observed | Not observed | Not observed | Not observed |
| Temperature limitation at the time of coating | | No | No | No | No | No | No | No | No | No | No |
| Mouth-feel of the film when the tablet is taken | | No problem | No problem | No problem | No problem | No problem | No problem | No problem | No problem | No problem | No problem |
| Bitterness of the film | | Not observed | Not observed | Not observed | Not observed | Not observed | Not observed | Not observed | Not observed | Not observed | Not observed |
| Hardness | Uncoated orally disintegrating tablet (kg) | 6.0 | 6.0 | 6.0 | 6.0 | 6.0 | 6.0 | 6.0 | 6.0 | 6.0 | 6.0 |
| | Coated orally disintegrating tablet (kg) | 6.6 | 6.5 | 6.4 | 9.1 | 7.2 | 8.0 | 6.5 | 6.4 | 6.4 | 9.5 |
| | Increasing ratio (%) | 10 | 8 | 7 | 52 | 20 | 33 | 8 | 7 | 7 | 58 |
| Dissolving time of the film (s) | | 6 - 7 | 4 - 5 | 4 - 5 | 4 - 5 | 3 - 4 | 4 - 5 | 4 - 5 | 4 - 5 | 4 - 5 | 6 - 7 |

FIG. 5

| | Additive | Example 14 Blending amount (mg) | Example 15 Blending amount (mg) | Example 16 Blending amount (mg) | Example 17 Blending amount (mg) | Example 18 Blending amount (mg) | Example 19 Blending amount (mg) | Example 20 Blending amount (mg) |
|---|---|---|---|---|---|---|---|---|
| Film base | HPMC | 2.27 | 2.27 | 2.27 | 2.27 | 2.27 | 2.27 | 2.27 |
| Plasticizer | Macrogol 400 | 2.27 | 2.27 | 2.27 | 2.27 | 2.27 | 2.27 | 2.27 |
| Corrigent | Sucralose | | 0.03 | 0.03 | 0.03 | 0.03 | 0.03 | 0.03 |
| Excipient | D-mannitol | | | 0.50 | | | | |
| | Erythritol | | | | 0.50 | | | |
| | Lactose hydrate | | | | | 0.50 | | |
| | Xylitol | | | | | | 0.50 | |
| | Isomalt | | | | | | | 0.50 |
| Disintegrant | Crospovidone | | | | | | | |
| Lubricant | Talc | 0.40 | 0.40 | 0.40 | 0.40 | 0.40 | 0.40 | 0.40 |
| Titanium dioxide | TiO$_2$ | 0.06 | 0.06 | 0.06 | 0.06 | 0.06 | 0.06 | 0.06 |
| Coloring agent | Yellow ferric oxide | | | | | | | |
| | Blue No. 2 Al lake | | | | | | | |
| Total | | 5.00 | 5.03 | 5.53 | 5.53 | 5.53 | 5.53 | 5.53 |
| Coatability | | Good | Good | Good | Good | Good | Good | Good |
| Pairing at the time of coating | | Not observed | Not observed | Not observed | Not observed | Not observed | Not observed | Not observed |
| Temperature limitation at the time of coating | | No | No | No | No | No | No | No |
| Mouth-feel of the film when the tablet is taken | | Unpleasant | Slightly unpleasant | Slightly unpleasant | Slightly unpleasant | Slightly unpleasant | Slightly unpleasant | Slightly unpleasant |
| Bitterness of the film | | Not observed | Not observed | Not observed | Not observed | Not observed | Not observed | Not observed |
| Hardness | Uncoated orally disintegrating tablet (kg) | 6.0 | 6.0 | 6.0 | 6.0 | 6.0 | 6.0 | 6.0 |
| | Coated orally disintegrating tablet (kg) | 6.7 | 6.4 | 6.9 | 6.5 | 6.8 | 6.9 | 7.0 |
| | Increasing ratio(%) | 12 | 7 | 15 | 8 | 13 | 15 | 17 |
| Dissolving time of the film (s) | | 7-8 | 7-8 | 7-8 | 6-7 | 6-7 | 6-7 | 6-7 |

FIG. 6

| Additive | | Blending amount (mg) | Blending amount (mg) | Blending amount (mg) | Blending amount (mg) |
|---|---|---|---|---|---|
| Film base | HPMC | 2.27 | 2.27 | 2.27 | 2.27 |
| Plasticizer | Macrogol 400 | 2.27 | 2.27 | 2.27 | 2.27 |
| Excipient | Erythritol | 0.50 | 0.50 | 0.50 | 0.50 |
| Disintegrant | Crospovidone | | 0.03 | 0.06 | 0.12 |
| Lubricant | Talc | 0.40 | 0.40 | 0.40 | 0.40 |
| Corrigent | Sucralose | 0.03 | 0.03 | 0.03 | 0.03 |
| Titanium dioxide | TiO₂ | 0.06 | 0.06 | 0.06 | 0.06 |
| Coloring agent | Yellow ferric oxide | | | Very small amount | Very small amount |
| | Blue No. 2 Al lake | | | Very small amount | Very small amount |
| Total | | 5.53 | 5.56 | 5.59 | 5.65 |
| Coatability | | Good | Good | Good | Good |
| Pairing at the time of coating | | Not observed | Not observed | Not observed | Not observed |
| Temperature limitation at the time of coating | | No | No | No | No |
| Mouth-feel of the film when the tablet is taken | | No problem | Slightly unpleasant | No problem | No problem |
| Bitterness of the film | | Not observed | Not observed | Not observed | Not observed |
| Hardness | Uncoated orally disintegrating tablet (kg) | 6.0 | 6.0 | 6.0 | 6.0 |
| | Coated orally disintegrating tablet (kg) | 6.5 | 6.9 | 6.6 | 6.8 |
| | Increasing ratio(%) | 8 | 15 | 10 | 13 |
| Disolving time of the film (s) | | 6 - 7 | 6 - 7 | 6 - 7 | 5 - 6 |

FIG. 7

| Additive | | Blending amount (mg) | Blending amount (mg) | Blending amount (mg) | Blending amount (mg) |
|---|---|---|---|---|---|
| Film base HPMC | Viscosity: 3.0mPa·s/Molecular weight: 16000 | 1.13 | | | |
| | Viscosity: 4.5mPa·s/Molecular weight: 22000 | | 1.13 | 1.13 | 2.36 |
| | Viscosity: 6.0mPa·s/Molecular weight: 35600 | | | | |
| Plasticizer | PG | 3.41 | 3.41 | 3.41 | 2.36 |
| Lubricant | Sucralose | 0.03 | 0.03 | 0.03 | 0.05 |
| Excipient | Erythritol | 0.50 | 0.50 | 0.50 | 0.75 |
| Disintegrant | Crospovidone | 0.06 | 0.06 | 0.06 | 0.09 |
| Lubricant | Talc | 0.40 | 0.40 | 0.40 | 0.60 |
| Titanium dioxide | TiO₂ | 0.06 | 0.06 | 0.06 | 2.25 |
| Coloring agent | Yellow ferric oxide | Very small amount | Very small amount | Very small amount | |
| | Blue No. 2 Al lake | Very small amount | Very small amount | Very small amount | |
| Total | | 5.59 | 5.59 | 5.59 | 8.46 |
| Coatability | | Good | Good | Good | Good |
| Pairing at the time of coating | | Not observed | Not observed | Not observed | Not observed |
| Temperature limitation at the time of coating | | No | No | No | No |
| Mouth-feel of the film when the tablet is taken | | No problem | No problem | No problem | No problem |
| Bitterness of the film | | Not observed | Not observed | Not observed | Not observed |
| Hardness | Uncoated orally disintegrating tablet (kg) | 6.0 | 6.0 | 6.0 | 6.0 |
| | Coated orally disintegrating tablet (kg) | 7.2 | 8.7 | 8.9 | 7.8 |
| | Increasing ratio(%) | 20 | 45 | 48 | 30 |
| Disolving time of the film (s) | | 3 - 4 | 4 - 5 | 5 - 6 | 5 - 6 |

ORALLY DISINTEGRATING TABLET COATED WITH FILM

CROSS REFERENCE TO RELATED APPLICATIONS

This application is based upon and claims the benefit of priority from the prior Japanese Patent Application No. 2014-024524, filed on Feb. 12, 2014, and PCT Application No. PCT/JP2015/053880, filed on Feb. 12, 2015, the entire contents of which are incorporated herein by reference.

FIELD

The present invention relates to an orally disintegrating tablet coated with film.

BACKGROUND

Orally disintegrating tablets are oral solid preparations that rapidly disintegrate in an oral cavity only in saliva in the oral cavity or a small amount of water in about 30 seconds or less. Since orally disintegrating tablets rapidly disintegrate in an oral cavity, the tablets are preparations that patients can easily take, and in particular, the needs of the elderly and children, who have difficulties in swallowing, for the tablets have been growing.

However, even immediately after produced, many orally disintegrating tablets generally have lower tablet hardness than typical oral solid preparations and are hygroscopic due to the influence of sugars, disintegrants, and other ingredients that are contained in the tablets in order to improve the disintegration property of the tablets. Therefore, many orally disintegrating tablets are difficult to store under high humidity conditions and to package in a single-dose pack.

Furthermore, generally, film coating over an oral solid preparation, such as a tablet and a granule, has been widely applied for the purpose of maintaining hardness and controlling hygroscopicity thereof. The film coating is applied for the purpose of protecting or stabilizing an active ingredient from environmental factors, such as humidity and light. Alternatively, the film coating is also applied for the purpose of giving moisture resistance to a tablet to maintain tablet hardness. Alternatively, the film coating is often applied for the purpose of masking the bitterness and odor of a pharmaceutical drug. Furthermore, in the case where an active ingredient is a hyperactive ingredient, such as an anticancer agent or an agent acting on hormone, it should be avoided that not only a distribution process, but also health care professionals on the front lines of health care are exposed to the hyperactive ingredient, and it is undesirable to unnecessarily expose a patient himself/herself to the hyperactive ingredient. Also in terms of safety measures against such exposure, the film coating is considered to be useful. Together with a proper amount of water, a patient takes such conventional film-coated oral solid preparation in the as-is status. That is, a conventional film-coated oral solid preparation is taken by a patient in a state in which a film coating layer of the preparation is not completely dissolved in the oral cavity of the patient.

As described above, many orally disintegrating tablets generally have lower tablet hardness than typical oral solid preparations and are hygroscopic, and therefore, the foregoing film coating technique is expected to be applied to orally disintegrating tablets, and actually, such application have gone through some trials. However, in the application of this film coating technique to orally disintegrating tablets, there are problems specific to orally disintegrating tablets. An orally disintegrating tablet coated with film needs to be such that a film coating layer thereof rapidly dissolves in the oral cavity of a patient, and subsequently, a body of the tablet also rapidly disintegrates. Furthermore, naturally, in the dissolution of the film coating layer of an orally disintegrating tablet coated with film in the oral cavity of a patient, the taste and mouth-feel also need to be considered.

Furthermore, orally disintegrating tablets have the property of rapidly dissolving with a small amount of water, and therefore, an orally disintegrating tablet coated with film needs a measure, for example, to prevent the tablet from disintegrating during a film coating process, and hence, the application of film coating to an orally disintegrating tablet is extremely difficult.

Japanese Patent Application Laid-Open No. 2001-192344 provides an oral solid preparation that is coated with a film coating agent wherein the blending weight ratio of methylcellulose to an acrylic polymer is from 5:95 to 60:40. Furthermore, Japanese Patent Application Laid-Open No. 2001-192344 describes a technique of coating granulation particles with said film coating agent, and then molding an uncoated orally disintegrating tablet. However, Japanese Patent Application Laid-Open No. 2001-192344 does not disclose a technique of applying film-coating to an orally disintegrating tablet itself. Furthermore, according to the description of Examples of Japanese Patent Application Laid-Open No. 2001-192344, in the particles of Examples coated by the foregoing technique, the time elapsed before bitterness was felt, that is, the time elapsed before a film coating layer dissolved was 30 seconds or more. Hence, in the case where the entire surface of an uncoated orally disintegrating tablet is film-coated with the film coating agent described in Examples of Japanese Patent Application Laid-Open No. 2001-192344, it is hard to expect that the film coating layer in the surface of the orally disintegrating tablet rapidly dissolves. Therefore, even if the film coating agent described in Japanese Patent Application Laid-Open No. 2001-192344 is applied to an orally disintegrating tablet, it is thought to be difficult to result in obtaining an orally disintegrating tablet coated with film having a rapid disintegration property.

Japanese Patent Application Laid-Open No. 2008-280316 describes that a dry-coated orally disintegrating tablet comprising an inner core and a coated layer is coated with a coating agent produced by adding Macrogol 6000 and titanium oxide to a cellulose derivative, such as hydroxymethyl propyl cellulose, hydroxymethyl cellulose, or methylcellulose.

Japanese Patent Application Laid-Open No. 2013-155148 describes a technique of film-coating an orally disintegrating tablet with a coating liquid in which a compound selected from polyvinyl-alcohol polymers and a discoloration-inducing metal oxide are dispersed in order to UV-laser-print characters and the like on the surface of the orally disintegrating tablet for the purpose of improving distinguishability.

However, according to the specification of Japanese Patent Application Laid-Open No. 2008-280316, the inventors of Japanese Patent Application Laid-Open No. 2008-280316 thought that common orally disintegrating tablets primarily have no sufficient hardness, and hence, film coating cannot be applied to such tablets, and therefore, the inventors produced a new preparation, that is, a dry-coated tablet capable of dissolving in an oral cavity. Furthermore, the technique described in Japanese Patent Application Laid-Open No. 2008-280316 is to coat the dry-coated tablet capable of dissolving in an oral cavity with the foregoing coating agent, and therefore, this technique cannot be applied to common orally disintegrating tablets. As for orally disintegrating tablets of Examples described in Japanese Patent Application Laid-Open No. 2013-155148, the time elapsed before an uncoated orally disintegrating tablet disintegrated in an oral cavity was approximately 30 seconds, in contrast, the time elapsed before a coated orally disintegrating tablet disintegrated in an oral cavity was approximately 60 seconds. Thus, a coating liquid described in Japanese Patent Application Laid-Open No. 2013-155148 has a practical problem because another 30 seconds is required for the oral disintegration due to the film coating.

WO 2010/113841 describes a stable coated orally disintegrating tablet containing a drug other than nalfurafine or a pharmaceutically acceptable salt thereof, wherein the tablet is coated with a coating layer containing a water-soluble substance and a polyvinyl alcohol resin, the coating layer having the weight ratio of the polyvinyl alcohol resin to the water-soluble substance of from 1:0.1 to 1:9, the water-soluble substance being at least one of maltose, maltitol, sorbitol, xylitol, fructose, glucose, lactitol, isomaltose, lactose, erythritol, mannitol, trehalose, and sucrose, dissolving in an amount of 1 g or more in less than 10 mL of water at 20° C., having a hydroxyl group in its molecule, and having a molecular weight of not more than 200 per unit hydroxyl group.

Japanese Patent Application Laid-Open No. 2010-248106 describes an orally disintegrating tablet coated with film comprising a film coating layer, the layer containing: at least one water-soluble polymer selected from the group consisting of hypromellose, hydroxypropylcellulose, water-soluble vinyl derivatives, and starches; and at least one plasticizer selected from the group consisting of polyethylene glycol, polysorbate, propylene glycol, triacetin, and triethyl citrate.

However, in WO 2010/113841 and Japanese Patent Application Laid-Open No. 2010-248106, although the dissolution time and plasticity of the film coating layer are considered, the feel of an orally disintegrating tablet when the tablet is taken, such as taste or mouth-feel, which is the most important for the tablet, and ease of production are not examined in detail.

After a patent application on which the present invention is based, WO 2014/157264 discloses an orally disintegrating tablet coated with film that contains at least one sweetener and is film-coated with at least one cellulose resin selected from methylcellulose, hypromellose, hydroxypropylcellulose, and hypromellose acetate succinate.

CITATION LIST

Patent Literature

Patent Literature 1: Japanese Patent Application Laid-Open No. 2001-192344
Patent Literature 2: Japanese Patent Application Laid-Open No. 2008-280316
Patent Literature 3: Japanese Patent Application Laid-Open No. 2013-155148
Patent Literature 4: WO 2010/113841
Patent Literature 5: Japanese Patent Application Laid-Open No. 2010-248106
Patent Literature 6: WO 2014/157264

SUMMARY

As described above, in the case where film coating is applied to an orally disintegrating tablet, a film coating layer of the tablet should not only rapidly dissolve, but also have a good taste and mouth-feel when the tablet is taken. On the other hand, there is a need to prevent, for example, a change in the appearance of the tablet, such as a crack in the film coating layer, and a decrease in tablet hardness even when the tablet is in an unpackaged state, in order that what is called single-dose packaging can be applied to the tablet. Furthermore, it is desired that a method of producing the tablet requires neither a special apparatus nor a complicated production process, and is simple as much as possible.

However, as described above, when conventional film coating is applied to an orally disintegrating tablet, the time elapsed before the tablet disintegrates in an oral cavity is often longer, and hence, it is not easy to solve all the foregoing problems. Therefore, there have so far been only a few examples of practical application of an orally disintegrating tablet coated with film, and hence, further studies have been needed.

An object of the present invention is to provide an orally disintegrating tablet coated with film that allows the time elapsed before a film thereof dissolves to be shorter, has a good feel when the tablet is taken, and is capable of being easily mass-produced.

According to an embodiment of the present invention, there is provided an orally disintegrating tablet coated with film, characterized in that the tablet is coated with a film coating composition, the film coating composition comprising: a water-soluble and ethanol-insoluble film coating base; and at least one plasticizer selected from the group consisting of propylene glycol and polyethylene glycol in a liquid or semisolid state at room temperature.

According to an embodiment of the present invention, there is provided an orally disintegrating tablet coated with film, characterized in that the tablet is coated with a film coating composition, the film coating composition comprising: a water-soluble and ethanol-insoluble film coating base; and at least one plasticizer selected from the group consisting of propylene glycol and polyethylene glycol in a liquid or semisolid state at room temperature, and containing the plasticizer in 10% by weight or more with respect to the weight of the film coating base.

In the orally disintegrating tablet, the film coating composition may further comprise an excipient and/or a disintegrant.

In the orally disintegrating tablet, the film coating base may be hypromellose.

In the orally disintegrating tablet, the polyethylene glycol may be Macrogol 200, Macrogol 300, Macrogol 400, Macrogol 600, Macrogol 1500, or Macrogol 1540.

BRIEF DESCRIPTION OF DRAWINGS

FIG. 1 shows the examination results on a film coating base of an orally disintegrating tablet coated with film according to an example of the present invention.

FIG. 2 shows the examination results on a plasticizer of an orally disintegrating tablet coated with film according to an example of the present invention.

FIG. 3 shows the examination results on the content ratio of a film coating base to a plasticizer in an orally disintegrating tablet coated with film according to an example of the present invention.

FIG. 4 shows the examination results on the content ratio of a film coating base to a plasticizer in an orally disintegrating tablet coated with film according to an example of the present invention.

FIG. 5 shows the examination results on an excipient of an orally disintegrating tablet coated with film according to an example of the present invention.

FIG. 6 shows the examination results on a disintegrant of an orally disintegrating tablet coated with film according to an example of the present invention.

FIG. 7 shows the examination results on the grade of hypromellose (also referred to as hydroxypropyl methylcellulose or HPMC) serving as a film coating base of an orally disintegrating tablet coated with film according to an example.

DESCRIPTION OF EMBODIMENTS

As a result of studies, the inventors found that the time elapsed before a film coating layer dissolves can be made sufficiently shorter by coating an orally disintegrating tablet with a film coating composition, the film coating composition comprising a water-soluble and ethanol-insoluble film coating base and a plasticizer in a liquid or semisolid state at room temperature and containing the plasticizer at a predetermined ratio with respect to the weight of the film coating base. Consequently, the inventors found that a good disintegration property and mouth-feel in an oral cavity can be achieved while holding the advantage of film coating at the same time, and thus the inventors completed the invention.

Hereinafter, an orally disintegrating tablet coated with film according to the present invention will be described in detail. It should be noted that the orally disintegrating tablet coated with film according to the present invention is not limited to the following embodiments and examples.

An orally disintegrating tablet coated with film according to the present invention is characterized in that the tablet is coated with a film coating composition, the film coating composition containing a water-soluble and ethanol-insoluble film coating base and a plasticizer in a liquid or semisolid state at room temperature. Furthermore, an orally disintegrating tablet coated with film according to the present invention is characterized in that the tablet is coated with a film coating composition, the film coating composition comprising a water-soluble and ethanol-insoluble film coating base and a plasticizer in a liquid or semisolid state at room temperature and containing the plasticizer in 10% by weight or more with respect to the weight of the film coating base.

(Film-Coating Composition)

In this specification, the term "ethanol insoluble" means slightly soluble, very slightly soluble, or practically insoluble or insoluble in ethanol, based on the section about solubility in the Japanese Pharmacopoeia, 16th Edition. As a water-soluble and ethanol-insoluble film coating base to be added to a film coating composition according to the present invention, for example, hypromellose (also referred to as hydroxypropyl methylcellulose or HPMC), polyvinyl alcohol (also referred to as PVA), and Kollicoat (registered trademark) IR, that is, a graft copolymer of polyvinyl alcohol and polyethylene glycol may be employed, but, the film coating base is not limited to these. The use of a water-soluble and ethanol-insoluble film coating base allows a film coating composition according to the present invention to have both a required tablet hardness and a shorter time elapsed before a film coating layer dissolves. In contrast, an ethanol-soluble film coating base is not suitable as a film coating base according to the present invention even if the base is water-soluble. As the film coating base to be used for the film coating composition according to the present invention, hypromellose is the most preferable.

Furthermore, in the case where hypromellose is employed as a film coating base for the film coating composition according to the present invention, the hypromellose may be suitably selected from hypromelloses having different grades (different viscosities of a 2% solution at 20° C. and molecular weights), in accordance with the quality required for an orally disintegrating tablet coated with film. For example, the use of hypromellose having Viscosity: 3.0 mPa·s/Molecular weight: 16000 (for example, TC-5E, Shin-Etsu Chemical Co., Ltd.) makes it possible to achieve rapid film dissolution. Furthermore, the use of hypromellose having Viscosity: 4.5 mPa·s/Molecular weight: 22000 (for example, TC-5M, Shin-Etsu Chemical Co., Ltd.) or hypromellose having Viscosity: 6.0 mPa·s/Molecular weight: 35600 (for example, TC-5R, Shin-Etsu Chemical Co., Ltd.) makes it possible to achieve both rapid film dissolution and excellent physical properties, such as increased hardness, of a preparation. A suitable combination of the grade and amount of these hypromelloses allows a wide range of quality of films to be obtained.

As the plasticizer to be added to the film coating composition according to the present invention, for example, at least one plasticizer selected from the group consisting of propylene glycol (also referred to as PG) and polyethylene glycol in a liquid or semisolid state at room temperature (also referred to as PEG) may be employed. In the specification, the term "semisolid" means the state of a Vaseline-like smooth solid. As the polyethylene glycol to be added to the film coating composition according to the present invention, Macrogol 200, Macrogol 300, Macrogol 400, Macrogol 600, Macrogol 1500, or Macrogol 1540 may be employed.

For the film coating composition according to the present invention, a plasticizer in a solid state at room temperature is not suitable in terms of mouth-feel at the time of taking the tablet. In the specification, the term "mouth-feel" means a slimy feel at the time of taking the tablet and the hardness of the film. Furthermore, triacetin and triethyl citrate have an unpleasant taste, and glycerin gives an unpleasant mouth-feel, and therefore, even if they are plasticizers in a liquid or semisolid state at room temperature, it is not preferable to use them alone as a plasticizer. However, triacetin, triethyl citrate, and glycerin may be added in combination with polyethylene glycol in a liquid or semisolid state at room temperature or propylene glycol.

When a film coating composition according to the present invention contains a plasticizer in 10% by weight or more with respect to the weight of a film coating base, the time elapsed before a film dissolves can be made sufficiently shorter, and, more preferably, the film coating composition contains a plasticizer in 100% by weight or more. A lower plasticizer content with respect to the film coating base causes the time elapsed before a film dissolves to be made longer, which is not preferable. Furthermore, in the film coating composition according to the present invention, the total weight of a film coating base and a plasticizer is preferably about 80% by weight with respect to the total weight of ingredients of the film coating composition, but is not limited to this. The total weight of a film coating base and a plasticizer is arbitrarily adjustable to the extent that a film can be formed.

The film coating composition according to the present invention may further contain at least one pharmaceutically acceptable additive selected from commonly-used excipients, disintegrants, lubricants, corrigents, and coloring agents. As an excipient, water-soluble sugars are preferable, and, for example, erythritol, D-mannitol, lactose hydrate, xylitol, isomalt, and maltose may be employed, but, the excipient is not limited to these. Furthermore, to the film coating composition according to the present invention, two or more excipients may be added in combination. The addition of these excipients makes it possible not only to give a refreshing effect and the like to a film coating layer, but also to promote the introduction of water at the time of taking the tablet. As a result, the film can still more rapidly dissolve. The excipient content of the film coating composition according to the present invention is not limited to particular values, but is arbitrarily adjustable to the extent that a film can be formed and a desired film strength can be obtained.

The disintegrant to be added to the film coating composition according to the present invention is only required to be pharmaceutically acceptable. As the disintegrant to be added to the film coating composition according to the present invention, for example, crospovidone, sodium starch glycolate, croscarmellose sodium, and low substituted hydroxypropylcellulose (also referred to as L-HPC) may be employed, but, the disintegrant is not limited to these.

The lubricant to be added to the film coating composition according to the present invention is only required to be pharmaceutically acceptable. As the lubricant to be added to the film coating composition according to the present invention, for example, talc, light anhydrous silicic acid, magnesium stearate, calcium stearate, sodium stearyl fumarate, and sucrose fatty acid esters may be employed, but, the lubricant is not limited to these. The lubricant content of the film coating composition according to the present invention is not particularly limited, but arbitrarily adjustable to the extent that a film can be formed.

The corrigent to be added to the film coating composition according to the present invention is only required to be pharmaceutically acceptable. As the corrigent to be added to the film coating composition according to the present invention, for example, sugars, such as sucrose, lactose, and glucose, sugar alcohols, such as mannitol, erythritol, xylitol, and sorbitol, sucralose, aspartame, acesulfame K, and thaumatin may be employed, but, the corrigent is not limited to these. The corrigent content of the film coating composition according to the present invention is not limited to particular values, but, the corrigent is added in small amounts, that is, in several percent by weight with respect to the total weight of additives constituting the film coating composition.

The coloring agent to be added to the film coating composition according to the present invention is only required to be pharmaceutically acceptable. As the coloring agent to be added to the film coating composition according to the present invention, for example, metal oxides, such as magnesium oxide, zinc oxide, aluminum oxide, anatase or rutile titanium dioxide, ferric oxide, and yellow ferric oxide, and water-soluble edible tar dyes, such as Food Yellow No. 5 and Food Blue No. 2, may be employed, but, the coloring agent is not limited to these.

(Uncoated Orally Disintegrating Tablet)

A tablet body of the orally disintegrating tablet coated with film according to the present invention, that is, an uncoated orally disintegrating tablet is not limited to particular tablets, but is a common orally disintegrating tablet. Furthermore, a well-known technique may be employed as a method for producing the tablet, and thus the production method is not limited to particular methods.

(Production Method)

A film coating composition is prepared by dissolving a film coating base and a plasticizer in a solvent, such as purified water. Besides, at this time, at least one pharmaceutically acceptable additive selected from excipients, disintegrants, lubricants, corrigents, and coloring agents may be added. In particular, sugars serving as excipients and disintegrants give a refreshing effect to a film coating layer and promote the introduction of water at the time of taking the tablet, thereby allowing the film to rapidly dissolve, and therefore, the excipients and disintegrants are preferably added to the film coating composition according to the present invention.

A method for applying film coating to an uncoated orally disintegrating tablet is not limited to particular methods, and may be such that an uncoated orally disintegrating tablet is fed into a general-purpose coating machine or sugar coating pan and a film-coating composition according to the present invention is added thereto.

As described above, the coating with a film coating composition having a specific composition gives sufficient tablet strength and stability to an orally disintegrating tablet coated with film according to the present invention and allows convenience in handling of the tablet to be improved. At the same time, in the orally disintegrating tablet coated with film according to the present invention, a film-coated portion of the tablet rapidly dissolves and a good mouth-feel is given, and also a good oral disintegration property is maintained. Furthermore, also in the case where an uncoated orally disintegrating tablet containing a hyperactive ingredient as an active ingredient, film-coating with the film-coating composition according to the present invention prevents the hyperactive ingredient from being exposed at the surface of the tablet, and thus prevents unnecessary exposure, and hence is useful also as a safety measure. Furthermore, the orally disintegrating tablet coated with film according to the present invention can be produced using not a special process and equipment, but a commonly used process and equipment for film coating.

EXAMPLES

The above-described orally disintegrating tablet coated with film according to the present invention will be described in more detail by way of specific examples and test results.

Reference Example

Method for Producing an Uncoated Orally Disintegrating Tablet 3.8 g of fexofenadine hydrochloride, 294.5 g of D-mannitol (P, Mitsubishi Shoji Foodtech Co., Ltd.), 45.0 g of low substituted hydroxypropylcellulose (L-HPC (21), Shin-Etsu Chemical Co., Ltd.), 7.5 g of aspartame (Ajinomoto Co., Inc.), and 1.4 g of powder hydrogenated maltose starch syrup (Amalty MR-50, Mitsubishi Shoji Foodtech Co., Ltd.) were fed into a high-speed stirring kneader (FLS-GS-2J, Fukae Powtec) and mixed, and then, 100 g of purified water was fed thereinto, and the resulting mixture was kneaded. The kneaded product was sieved through a sieve No. 8, and then dried in a shelf dryer (40C, Nikku Industry Co., Ltd.). The dried product was fed into a particle size regulator (P-04-S, Dalton Co., Ltd.) to undergo particle size regulation. The particle size regulated product was mixed with 11.3 g of crospovidone (CL-F, BASF), 3.8 g of light anhydrous silicic acid (Adsolider 101, Freund Corporation), 0.4 g of a flavor, and 7.5 g of sodium stearyl fumarate (PRUV, JRS Pharma) to obtain a mixture for tableting. The mixture for tableting was tableted using a tableting machine (VELA5, Kikusui Seisakusho Ltd.) so as to obtain an uncoated orally disintegrating tablet having a weight of 250 mg and a hardness of 6.0 kg.

Example 1

As Example 1, a film-coating composition was prepared using hypromellose (HPMC) as a film coating base. The film-coating composition was obtained in such a manner that hypromellose (TC-5E, Shin-Etsu Chemical Co., Ltd.), Macrogol 400 (NOF Corporation) as a plasticizer, erythritol (B Food Science Co., Ltd.) as an excipient, crospovidone (CL-F, BASF) as a disintegrant, talc (Fuji Talc Industrial Co., Ltd.) as a lubricant, sucralose (P, San-Ei Gen F.F.I., Inc.) as a corrigent, and titanium oxide (KA-10M, Titan Kogyo, Ltd.) and a very small amount of yellow ferric oxide and Blue No. 2 Al lake as coloring agents were dissolved and dispersed in purified water so as to achieve the formulation ratio shown in FIG. 1. An uncoated orally disintegrating tablet (Hardness: 6.0 kg) having a weight of 250 mg was prepared in accordance with Reference Example, and, using a coating machine (HC-LABO20, Freund Corporation), the uncoated orally disintegrating tablet was coated with the film-coating composition so as to achieve a predetermined weight, whereby an orally disintegrating tablet coated with film of Example 1 was produced.

Example 2

As Example 2, a film-coating composition was prepared using polyvinyl alcohol (PVA) as a film coating base. An orally disintegrating tablet coated with film was produced in the same manner as in Example 1 except that polyvinyl alcohol (EG-05, The Nippon Synthetic Chemical Industry Co., Ltd.) was added to purified water.

Example 3

As Example 3, a film-coating composition was prepared using Kollicoat (registered trademark) IR as a film coating base. An orally disintegrating tablet coated with film was produced in the same manner as in Example 1 except that Kollicoat (registered trademark) IR (BASF) was added to purified water.

Comparative Example 1

As Comparative Example 1, a film-coating composition was prepared using hydroxypropylcellulose (HPC) as a film coating base. An orally disintegrating tablet coated with film was produced in the same manner as in Example 1 except that hydroxypropylcellulose (SSL, Nippon Soda Co., Ltd.) was added to purified water.

Comparative Example 2

As Comparative Example 2, a film-coating composition was prepared using polyvinylpyrrolidone (PVP) as a film coating base. An orally disintegrating tablet coated with film was produced in the same manner as in Example 1 except that polyvinylpyrrolidone (K-30, DKS Co. Ltd.) was added to purified water.

For the orally disintegrating tablet coated with films of Examples 1 to 3 and Comparative Examples 1 and 2, a visual evaluation of manufacturability, a sensory test, a measurement of hardness, and a measurement of film dissolution time were performed.

(Visual Evaluation of Manufacturability)

The pairing (sticking) between tablets caused at the time of applying a coating to uncoated orally disintegrating tablets was visually evaluated. Tablets in which pairing was observed were considered to have a significant problem in suitability for a coating process, and therefore, it was determined that the coatability (manufacturability) of the tablets was not acceptable.

(Evaluation of Bitterness and Mouth-Feel of Film By Sensory Test)

Sensory tests were performed for orally disintegrating tablet coated with films, and (1) the presence of bitterness was evaluated, and (2) the mouth-feel during film dissolution was evaluated on three grades, that is, unpleasant, slightly unpleasant, and no problem.

(Tablet Hardness)

The hardness of the tablets was measured using a tablet hardness tester (DC-50, Okada Seiko Co., Ltd.).

(Evaluation of Film Dissolution Time By Sensory Test)

Sensory tests of an orally disintegrating tablet coated with film and an uncoated orally disintegrating tablet were performed to measure the time elapsed before the respective tablets dissolved in an oral cavity. The difference between the time elapsed before the orally disintegrating tablet coated with film dissolved in an oral cavity and the time elapsed before the uncoated orally disintegrating tablet dissolved in an oral cavity was regarded as a film dissolution time and evaluated.

The evaluation results of the orally disintegrating tablet coated with films of Examples 1 to 3 and Comparative Examples 1 and 2 are summarized in FIG. 1. The results in FIG. 1 revealed that the tablets of Examples 1 to 3 wherein a water-soluble and ethanol-insoluble film coating base was employed had good manufacturability and a good mouth-feel at the time of taking the tablets, and the hardness of the tablets was increased because of film coating and the film solubility thereof was good. In contrast, in Comparative Examples 1 and 2 wherein a water-soluble but ethanol-soluble film coating base was employed, the pairing was caused at the time of coating, whereby no film layer was formed.

Example 4

Next, an examination of plasticizers was performed. As Example 4, a film-coating composition was prepared using Macrogol 1500 as a plasticizer. An orally disintegrating tablet coated with film was produced in the same manner as in Example 1 except that Macrogol 1500 (polyethylene glycol #1500, NACALAI TESQUE, INC.) was added to purified water.

Example 5

As Example 5, a film-coating composition was prepared using propylene glycol (PG) as a plasticizer. An orally disintegrating tablet coated with film was produced in the same manner as in Example 1 except that propylene glycol (Wako Pure Chemical Industries, Ltd.) was added to purified water.

Comparative Example 3

As Comparative Example 3, a film-coating composition was prepared using Macrogol 6000 as a plasticizer. An orally disintegrating tablet coated with film was produced in the same manner as in Example 1 except that Macrogol 6000 (NOF Corporation) was added to purified water.

Comparative Example 4

As Comparative Example 4, a film-coating composition was prepared using triacetin as a plasticizer. An orally disintegrating tablet coated with film was produced in the same manner as in Example 1 except that triacetin (Wako Pure Chemical Industries, Ltd.) was added to purified water.

Comparative Example 5

As Comparative Example 5, a film-coating composition was prepared using triethyl citrate as a plasticizer. An orally disintegrating tablet coated with film was produced in the same manner as in Example 1 except that triethyl citrate (Morimura Bros., Inc.) was added to purified water.

Comparative Example 6

As Comparative Example 6, a film-coating composition was prepared using glycerin as a plasticizer. An orally disintegrating tablet coated with film was produced in the same manner as in Example 1 except that glycerin (Wako Pure Chemical Industries, Ltd.) was added to purified water.

Comparative Example 7

As Comparative Example 7, a film-coating composition was prepared using D-sorbitol as a plasticizer. An orally disintegrating tablet coated with film was produced in the same manner as in Example 1 except that D-sorbitol (Wako Pure Chemical Industries, Ltd.) was added to purified water.

Comparative Example 8

As Comparative Example 8, a film-coating composition was prepared using D-sorbitol as a plasticizer so as to set the blending ratio of hypromellose to D-sorbitol at 1:3. An orally disintegrating tablet coated with film was produced in the same manner as in Example 1 except that hypromellose (TC-5E, Shin-Etsu Chemical Co., Ltd.) and D-sorbitol (Wako Pure Chemical Industries, Ltd.) were added to purified water, and the blending ratio of hypromellose to the plasticizer was changed.

The evaluation results of the orally disintegrating tablet coated with films of Examples 1, 4, and 5 and Comparative Examples 3 to 8 are summarized in FIG. 2. The results shown in FIG. 2 revealed that the tablets of Examples 1, 4, and 5 wherein a plasticizer in a liquid or semisolid state at room temperature was employed had good manufacturability, and had an increased hardness by film coating and good film solubility. Furthermore, the tablets of Examples 1, 4, and 5 had a good mouth-feel at the time of taking the tablets. In contrast, the tablet of Comparative Example 3 wherein a plasticizer in a solid state at room temperature was employed had an unpleasant mouth-feel of the film. Furthermore, the tablets of Comparative Examples 4 and 5 had bitterness and an unpleasant mouth-feel, wherein triacetin or triethyl citrate was employed, even if they were plasticizers in a liquid or semisolid state at room temperature. The tablet of Comparative Example 6 wherein glycerin was employed had an unpleasant mouth-feel. Furthermore, the tablet of Comparative Example 7 wherein D-sorbitol was employed had a poor mouth-feel, and when the blending ratio of hypromellose to D-sorbitol was changed, the pairing was caused at the time of coating, whereby no film layer was formed (Comparative Example 8).

Next, by taking Macrogol 400 as an example, the lower limit of the plasticizer content was examined. Hypromellose (TC-5E, Shin-Etsu Chemical Co., Ltd.) and Macrogol 400 (NOF Corporation) as a plasticizer were added to purified water so as to achieve the formulation ratio shown in FIG. 3. In the mixture, talc (Fuji Talc Industrial Co., Ltd.) as a lubricant and titanium oxide (KA-10M, Titan Kogyo, Ltd.) were dissolved and dispersed to prepare a film-coating composition. An uncoated orally disintegrating tablet (Hardness: 6.0 kg) having a weight of 250 mg was prepared, and, using a coating machine (HC-LABO20, Freund Corporation), the uncoated orally disintegrating tablet was coated with the prepared film-coating composition to produce an orally disintegrating tablet coated with film.

The examination results on the plasticizer content are summarized in FIG. 3. The results shown in FIG. 3 revealed that a higher content of plasticizer allowed the solubility of a film to be dose-dependently improved. When a film coating composition contained a plasticizer in 10% by weight or more with respect to the weight of a film coating base, the time elapsed before a film dissolved was controlled to within 10 seconds.

Example 6

Next, a further examination of the ratio of a plasticizer to a film coating base was performed. The examination was performed using hypromellose as a film coating base, and using Macrogol 400 or propylene glycol, or a combination of glycerin and Macrogol 400 or propylene glycol as a plasticizer. As Example 6, an orally disintegrating tablet coated with film was produced in the same manner as in Example 1 except that hypromellose (TC-5E, Shin-Etsu Chemical Co., Ltd.) and Macrogol 400 (NOF Corporation) as a plasticizer were added to purified water and the blending ratio of the plasticizer to the film coating base was changed.

Example 7

As Example 7, an orally disintegrating tablet coated with film was produced in the same manner as in Example 1 except that hypromellose (TC-5E, Shin-Etsu Chemical Co., Ltd.), and Macrogol 400 (NOF Corporation) and glycerin (Wako Pure Chemical Industries, Ltd.) as plasticizers were added to purified water and the blending ratio of the plasticizers to the film coating base was changed.

Example 8

As Example 8, an orally disintegrating tablet coated with film was produced in the same manner as in Example 1 except that hypromellose (TC-5E, Shin-Etsu Chemical Co., Ltd.) and propylene glycol (Wako Pure Chemical Industries, Ltd.) as a plasticizer were added to purified water and the blending ratio of the plasticizer to the film coating base was changed.

Example 9

As Example 9, an orally disintegrating tablet coated with film was produced in the same manner as in Example 1 except that hypromellose (TC-5E, Shin-Etsu Chemical Co., Ltd.), and propylene glycol (Wako Pure Chemical Industries, Ltd.) and glycerin (Wako Pure Chemical Industries, Ltd.) as plasticizers were added to purified water and the blending ratio of the plasticizers to the film coating base was changed.

Example 10

As Example 10, an orally disintegrating tablet coated with film was produced in the same manner as in Example 1 except that hypromellose (TC-5E, Shin-Etsu Chemical Co., Ltd.), and propylene glycol (Wako Pure Chemical Industries, Ltd.) and glycerin (Wako Pure Chemical Industries, Ltd.) as plasticizers were added to purified water and the blending ratio of the plasticizers to the film coating base was changed.

Example 11

As Example 11, an orally disintegrating tablet coated with film was produced in the same manner as in Example 1 except that hypromellose (TC-5E, Shin-Etsu Chemical Co., Ltd.), and propylene glycol (Wako Pure Chemical Industries, Ltd.) and glycerin (Wako Pure Chemical Industries, Ltd.) as plasticizers were added to purified water and the blending ratio of the plasticizers to the film coating base was changed.

Example 12

As Example 12, an orally disintegrating tablet coated with film was produced in the same manner as in Example 1 except that hypromellose (TC-5E,
Shin-Etsu Chemical Co., Ltd.), and propylene glycol (Wako Pure Chemical Industries, Ltd.) as a plasticizer were added to purified water, and furthermore, maltose (PH, Hayashibara Co., Ltd.) was added thereto as an excipient.

Example 13

As Example 13, an orally disintegrating tablet coated with film was produced in the same manner as in Example 1 except that hypromellose (TC-5E, Shin-Etsu Chemical Co., Ltd.), and propylene glycol (Wako Pure Chemical Industries, Ltd.) as a plasticizer were added to purified water and the blending ratio of the plasticizer to the film coating base was changed.

The examination results on plasticizer content are summarized in FIG. 4. The results shown in FIG. 4 revealed that an increase in plasticizer content with respect to film coating base content makes rapid film dissolution possible. Furthermore, the results revealed that glycerin is not preferably used alone as a plasticizer, but, when glycerin is used in combination with polyethylene glycol or propylene glycol, such use does not cause a problem in mouth-feel. Furthermore, when maltose was added in the same amount as a plasticizer, a film coating layer capable of rapidly dissolving and having a good mouth-feel and providing a pleasant feel at the time of taking the tablet was obtained. Furthermore, the results of Example 13 revealed that the use of a film-coating composition containing a plasticizer in 20% by weight or more with respect to the weight of a film coating base allows an orally disintegrating tablet coated with film having good manufacturability, an increased hardness by film coating, and good film solubility to be obtained.

Example 14

Next, an examination on excipients was performed. A film-coating composition was prepared using hypromellose (HPMC) as a film coating base and using Macrogol 400 as a plasticizer. The film-coating composition was obtained in such a manner that hypromellose (TC-5E, Shin-Etsu Chemical Co., Ltd.), Macrogol 400 (NOF Corporation) as a plasticizer, talc (Fuji Talc Industrial Co., Ltd.) as a lubricant, and titanium oxide (KA-10M, Titan Kogyo, Ltd.) as a coloring agent were dissolved and dispersed in purified water so as to achieve the formulation ratio shown in FIG. 5. An uncoated orally disintegrating tablet (Hardness: 6.0 kg) having a weight of 250 mg was prepared in accordance with Reference Example, and, using a coating machine (HC-LABO20, Freund Corporation), the uncoated orally disintegrating tablet was coated with the film-coating composition so as to achieve a predetermined weight, whereby an orally disintegrating tablet coated with film of Example 14 was produced.

Example 15

As Example 15, hypromellose (TC-5E, Shin-Etsu Chemical Co., Ltd.), Macrogol 400 (NOF Corporation) as a plasticizer, talc (Fuji Talc Industrial Co., Ltd.) as a lubricant, sucralose (P, San-Ei Gen F.F.I., Inc.) as a corrigent, and titanium oxide (KA-10M, Titan Kogyo, Ltd.) as a coloring agent were dissolved and dispersed in purified water so as to achieve the formulation ratio shown in FIG. 5, whereby a film-coating composition was obtained. An uncoated orally disintegrating tablet (Hardness: 6.0 kg) having a weight of 250 mg was prepared in accordance with Reference Example, and, using a coating machine (HC-LABO20, Freund Corporation), the uncoated orally disintegrating tablet was coated with the film-coating composition so as to achieve a predetermined weight, whereby an orally disintegrating tablet coated with film of Example 15 was produced.

Example 16

As Example 16, hypromellose (TC-5E, Shin-Etsu Chemical Co., Ltd.), Macrogol 400 (NOF Corporation) as a plasticizer, D-mannitol (P, Mitsubishi Shoji Foodtech Co., Ltd.) as an excipient, talc (Fuji Talc Industrial Co., Ltd.) as a lubricant, sucralose (P, San-Ei Gen F.F.I., Inc.) as a corrigent, and titanium oxide (KA-10M, Titan Kogyo, Ltd.) as a coloring agent were dissolved and dispersed in purified water so as to achieve the formulation ratio shown in FIG. 5, whereby a film-coating composition was obtained. An uncoated orally disintegrating tablet (Hardness: 6.0 kg) having a weight of 250 mg was prepared in accordance with Reference Example, and, using a coating machine (HC-LABO20, Freund Corporation), the uncoated orally disintegrating tablet was coated with the film-coating composition so as to achieve a predetermined weight, whereby an orally disintegrating tablet coated with film of Example 16 was produced.

Example 17

As Example 17, a film-coating composition was prepared using erythritol as an excipient. An orally disintegrating tablet coated with film was produced in the same manner as in Example 16 except that erythritol (B Food Science Co., Ltd.) was added to purified water.

Example 18

As Example 18, a film-coating composition was prepared using lactose hydrate as an excipient. An orally disintegrating tablet coated with film was produced in the same manner as in Example 16 except that lactose hydrate (200M, DMV) was added to purified water.

Example 19

As Example 19, a film-coating composition was prepared using xylitol as an excipient. An orally disintegrating tablet coated with film was produced in the same manner as in Example 16 except that xylitol (ROQUETTE) was added to purified water.

Example 20

As Example 20, a film-coating composition was prepared using isomalt as an excipient. An orally disintegrating tablet coated with film was produced in the same manner as in Example 16 except that isomalt (galenIQ810, BENEO-Palatinit) was added to purified water.

The examination results on the excipients are summarized in FIG. 5. The results shown in FIG. 5 revealed that the use of any of the sugars or the sugar alcohols as an excipient allows the tablet to have good manufacturability, an increased hardness by film coating, and good film solubility. It was confirmed that, also in the case of using xylitol or isomalt, which is slightly highly hygroscopic, there was no problem in the manufacturability of the tablet and the physical properties immediately after the tablet was produced.

Next, an examination on disintegrant content was performed. Hypromellose (TC-5E, Shin-Etsu Chemical Co., Ltd.) as a film coating base, Macrogol 400 (NOF Corporation) as a plasticizer, and erythritol (B Food Science Co., Ltd.) as an excipient were dissolved in purified water so as to achieve the formulation ratio shown in FIG. 6. As a disintegrant, a predetermined amount of crospovidone (CL-F, BASF) was added to the mixture. Furthermore, talc (Fuji Talc Industrial Co., Ltd.) as a lubricant, sucralose (P, San-Ei Gen F.F.I., Inc.) as a corrigent, and titanium oxide (KA-10M, Titan Kogyo, Ltd.) and a very small amount of yellow ferric oxide and Blue No. 2 Al lake as coloring agents were dissolved and dispersed in the mixture, whereby a film-coating composition was obtained. An uncoated orally disintegrating tablet (Hardness: 6.0 kg) having a weight of 250 mg was prepared, and, using a coating machine (HC-LABO20, Freund Corporation), the uncoated orally disintegrating tablet was coated with the prepared film-coating composition to produce an orally disintegrating tablet coated with film.

The examination results on disintegrant content are summarized in FIG. 6. The results shown in FIG. 6 revealed that the addition of the disintegrant brought about an improvement in film solubility.

Finally, an examination on hypromellose grade was performed. As hypromellose, three types, namely, TC-5E (Viscosity of a 2% solution at 20° C.: 3.0 mPa·s/Molecular weight: 16000), TC-5M (Viscosity of a 2% solution at 20° C.: 4.5 mPa·s/Molecular weight: 22000) and TC-5R (Viscosity of a 2% solution at 20° C.: 6.0 mPa·s/Molecular weight: 35600), each manufactured by Shin-Etsu Chemical Co., Ltd., were used. Hypromellose as a film coating base, propylene glycol (Wako Pure Chemical Industries, Ltd.) as a plasticizer, and erythritol (B Food Science Co., Ltd.) as an excipient were dissolved in purified water so as to achieve the formulation ratio shown in FIG. 7. As a disintegrant, crospovidone (CL-F, BASF) was added to the mixture, and furthermore, talc (Fuji Talc Industrial Co., Ltd.) as a lubricant, sucralose (P, San-Ei Gen F.F.I., Inc.) as a corrigent, and titanium oxide (KA-10M, Titan Kogyo, Ltd.) and a very small amount of yellow ferric oxide and Blue No. 2 Al lake as coloring agents were dissolved and dispersed in the mixture, whereby a film-coating composition was obtained. An uncoated orally disintegrating tablet (Hardness: 6.0 kg) having a weight of 250 mg was prepared, and, using a coating machine (HC-LABO20, Freund Corporation), the uncoated orally disintegrating tablet was coated with the prepared film-coating composition to produce an orally disintegrating tablet coated with film.

The examination results on hypromellose grade are summarized in FIG. 7. The results shown in FIG. 7 revealed that the use of TC-5E brings about rapid film dissolution. Furthermore, it was revealed that the use of TC-5M or TC-5R brings about excellent physical properties of a preparation as well as rapid film dissolution. Furthermore, it was revealed that, even when the titanium oxide content of a film-coating composition is increased, no problem arises in the film solubility and physical properties of a preparation.

According to the present invention, an orally disintegrating tablet coated with film that brings about a shorter film dissolution time is provided. Furthermore, an orally disintegrating tablet coated with film that a patient can easily take because of its taste, mouth-feel, and the like is provided. Furthermore, an orally disintegrating tablet coated with film capable of being easily mass-produced is provided.

The invention claimed is:

1. A tablet consisting of:
   an uncoated tablet; and
   a film coating the uncoated tablet,
   wherein
   the film contains hypromellose, propylene glycol, an excipient, and at least one pharmaceutically acceptable additive selected from the group consisting of a disintegrant, a lubricant, a corrigent and a coloring agent,
   the excipient is selected from the group consisting of erythritol, D-mannitol, lactose hydrate, xylitol, isomalt, maltose and a combination thereof, and
   the propylene glycol is contained more than 100% by weight with respect to a weight of the hypromellose.

2. The tablet according to claim 1, wherein the propylene glycol is contained less than 301.8% by weight with respect to the weight of the hypromellose.

3. The tablet according to claim 1, wherein the hypromellose is selected from the group consisting of a hypromellose having Viscosity: 3.0 mPa·s/Molecular weight: a hypromellose having Viscosity: 4.5 mPa·s/Molecular weight: 22000 and a hypromellose having Viscosity: 6.0 mPa·s/Molecular weight: 35600.

4. The tablet according to claim 1, wherein the disintegrant is selected from the group consisting of crospovidone, sodium starch glycolate, croscarmellose sodium and low substituted hydroxypropylcellulose.

* * * * *